United States Patent

Krumhar et al.

[11] Patent Number: 5,096,813
[45] Date of Patent: Mar. 17, 1992

[54] VISUAL INDICATOR SYSTEM

[75] Inventors: Kim C. Krumhar, Bedford, Tex.; Marcus Karel, Newton, Mass.

[73] Assignee: Massachusetts Institute of Technology, Cambridge, Mass.

[21] Appl. No.: 403,179

[22] Filed: Sep. 5, 1989

Related U.S. Application Data

[63] Continuation-in-part of Ser. No. 220,499, Jul. 18, 1988, abandoned, which is a continuation of Ser. No. 879,920, Jun. 30, 1986, abandoned.

[51] Int. Cl.[5] .......................... C12Q 1/28; C12Q 1/26; G01N 31/22
[52] U.S. Cl. .......................... 435/28; 422/56; 422/57; 422/58; 422/61; 426/87; 426/232; 435/25; 435/805; 435/810; 436/1; 436/2; 436/127; 436/136; 436/138; 436/904
[58] Field of Search .................. 422/58, 61, 56–57; 435/7, 29, 291, 805, 810, 28, 25; 436/1, 2, 127, 904, 136, 138; 426/232, 87

[56] References Cited

U.S. PATENT DOCUMENTS

| 4,120,658 | 10/1978 | Bruttig ........................ 436/68 |
| 4,169,811 | 10/1979 | Yoshikawa et al. ............ 436/136 X |
| 4,447,542 | 5/1984 | Gantzner ..................... 436/904 X |
| 4,526,752 | 7/1985 | Perlman et al. ................ 436/1 X |

FOREIGN PATENT DOCUMENTS 49-16513  4/1974  Japan ............................ 436/1

OTHER PUBLICATIONS

Allied Corp. "The Breakthrough in Freshness and Distribution Control", (1984).

*Primary Examiner*—Jill Johnston
*Attorney, Agent, or Firm*—Bruce Jacobs

[57] ABSTRACT

Packages which are subject to tampering while in a store or deterioration over time due to the presence of oxygen may be readily identified by placing therein a multi-component visual indicator system which is sensitive to the presence of oxygen. The system, which may be prepared aerobically and then placed into an anaerobic environment for use, is not effected by the presence of reducing agents found commonly in foods, drugs, and cosmetics.

22 Claims, 3 Drawing Sheets

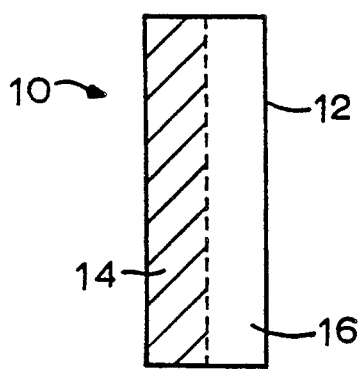
FIG. 1
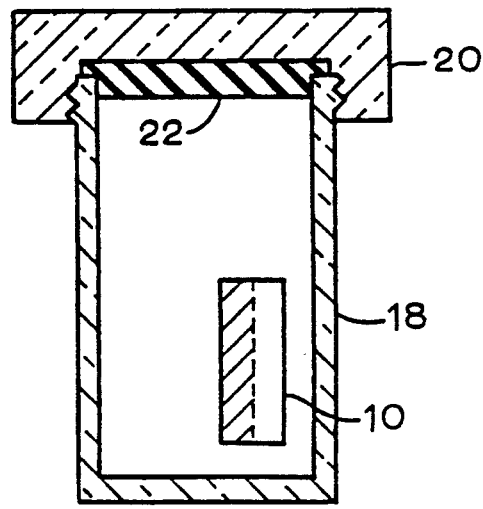
FIG. 2
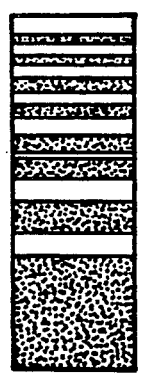 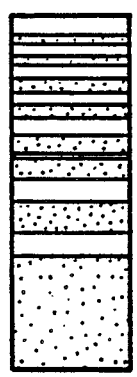
FIG. 3A  FIG. 3B
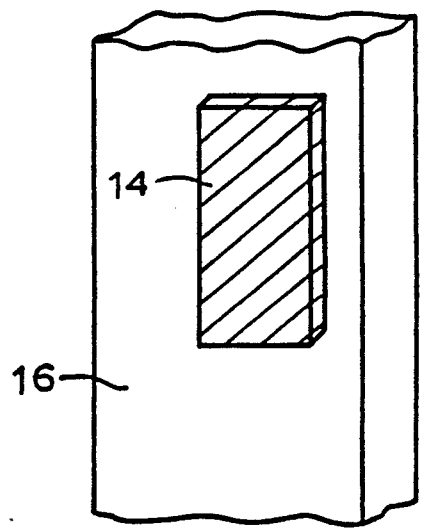
FIG. 4

VISUAL INDICATOR SYSTEM

CROSS REFERENCE TO RELATED APPLICATIONS

This application is a continuation-in-part of U.S. Ser. No. 220,499, filed July 18, 1988, which is a continuation of U.S. Ser. No. 879,920, filed June 30, 1986, now abandoned.

TECHNICAL FIELD

This invention relates to a visual indicator system for detecting loss of package integrity when the contents thereof, optionally including reducing agents, in an anaerobic environment are exposed to atmospheric oxygen. It relates particularly to packages of food, drugs, cosmetics, medical, and other products which can be compromised by tampering or exposure to the atmosphere or which may deteriorate relatively slowly due to the presence of oxygen, and a system which can provide a readily recognized warning of such tampering, exposure or deterioration by casual inspection so that such packages can be safely discarded prior to causing harm to a purchaser/consumer.

BACKGROUND OF THE INVENTION

Enormous quantities of over-the-counter drugs, cosmetics and packaged food products are produced each year for sale in sealed, shelf-stable containers. A small fraction of this production although manufactured properly fails to reach the consumer intact due to tampering or oxidative degradation. Manufacturers faced with preventing tampering have reacted by adopting a number of simple methods for providing tamper evidence to consumers and merchants. Methods commonly employed include the use of innerseals, vacuum indicators, shrinkwrap bands, film overwraps, breakaway cap rings, and other physical indicators of package integrity. Many of these methods suffer from one or more weaknesses making them vulnerable to failure at the hands of a determined individual or through lack of consumer awareness.

A number of colorimetric package integrity sensors have been reported which are designed to show a color change after a package seal is broken and the contents exposed to the atmosphere. Factors used to cause such color changes have included moisture, loss of headspace gas, and atmospheric oxygen. Of these factors, only oxygen appears to be a relatively constant indicator since it is present at about 21% of the earth's atmosphere. Thus it has been used as a basis for colorimetric reactions in package integrity testing.

For instance, Perlman et al. in U.S. Pat. No. 4,526,752 teaches the use of redox indicator dyes, i.e. methylene blue reduced to their colorless leuco forms, as oxygen indicators for the detection of tampering. The decolorized form of methylene blue turns blue very rapidly in the presence of or after exposure to oxygen. Perlman et al. teaches that the development of color, which is caused by an influx of oxygen after the package seal is broken, may be reversed when a reducing agent is present and the package is returned to an oxygen-free atmosphere. Moreover, the presence of reducing agents in the product contained in the package can adversely effect the shelf stability of the indicator and can interfere with designed operation of the system.

A similar system using redox indicator dyes such as methylene blue is disclosed in Yoshikawa et al. in U.S. Pat. Nos. 4,169,811 and 4,349,509.

Food, drug, and cosmetic systems typically contain varying amounts of common reducing agents such as glucose, fructose, maltose, lactose, sodium or zinc dithionite, ferrous sulfate, ferrous chloride, ferrous ammonium sulfate, ferrous oxalate, ferrous lactate, iron sulfide, ascorbic acid, sodium ascorbate, stannous chloride, and numerous other compounds. These reducing agents are prone to causing interference in the critical reaction leading to the formation of the colored dye products from colorless leuco-form redox compounds. Alternatively, the reducing agents in the product could cause the colored dye to revert to its colorless leuco form even after exposure to oxygen, thereby yielding false negative results. Thus, a major limitation to the use of the Perlman et al. and Yoshikawa et al. sensors is that they can not be used with those packaged products which contain reducing agents. This effectively precludes their use with most products derived from natural sources, many vitamin preparations, and some cosmetics.

Another serious limitation of the redox systems is that the conversion from leuco to color is extremely sensitive to oxygen. Thus, the reaction occurs so quickly that the sensor must be prepared, incorporated into the package, and the package sealed under completely anaerobic conditions. As a result production of packages incorporating the leuco dye sensors is inconvenient, costly, complicated, and is limited to "batch" operations characterized by low speed and efficiency.

Other sensors have been based upon causing a color change. For instance, U.S. Pat. No. 3,899,295 describes a sensor wherein a pH indicator is placed in an environment filled with an acidic or basis gas, e.g. carbon dioxide or ammonia. This indicator requires the use of reactive gases which are known to interact and combine with many components of food, drug, and cosmetic systems. As such, the sensor can affect the nutritional, sensory, and esthetic properties of materials packaged with it via chemical reaction. Another colorimetric sensor is a time-temperature sensor Lifelines ® of Allied Chemical which allows a user to estimate the total heat exposure load on the sensor and attached sample. The product is composed of a monomer that polymerizes in response to heat. Also Fisher Scientific markets an indicating silica gel useful in gauging the extent to which a dry material has become hydrated over time. Also Metrohm of Switzerland has a sensor to evaluate the development of rancidity in fats and oils while in use. While the sensor works upon an oxidation system, it does not use a colorimetric system and is not useful to determine integrity of sealed packages.

It is accordingly an object of the present invention to produce a visual indicator system to readily determine loss of product integrity of an apparently sealed package. It is a further object to produce a colorimetric test having an irreversible dramatic color change. It is a still further object to produce a sensor which may be prepared aerobically and then inserted into an anaerobic environment for use. It is a still further object to produce a sensor which is unaffected by the presence of reducing agents such as are routinely incorporated in many, many commercial products. It is a still further object to produce a test which is sufficiently sensitive to show evidence of tampering within about 1 to 8 hours, but is also sufficiently insensitive that it may be prepared in an aerobic environment and then transferred into an anaerobic environment for use. It is a still further object to produce a sensor in the form of a machine-readable universal bar code which will become unreadable after exposure of it to oxygen. These and other objects will be apparent from the ensuing description.

These and other objects of the present invention are obtained by means of a colorimetric indicator system which becomes operative in the presence of oxygen and comprises a color indicator in combination with one or more oxygen-sensitive compounds which upon exposure to oxygen will cause the color indicator to change color but which is unaffected by contact with reducing agents. The presence of oxygen produces a color change in the indicator, while the absence of oxygen precludes such a change. The system is completely functional both in the presence or absence of reducing agents in the products being protected.

BRIEF DESCRIPTION OF THE DRAWINGS

FIG. 1 shows a single color indicator strip of the present invention.

FIG. 2 shows a package containing the strip of FIG. 1.

FIG. 3A shows a sensor of the present invention in the form of a readable bar code and FIG. 3B shows the same sensor after contamination with atmospheric oxygen.

FIG. 4 shows a variation of the strip of FIG. 1 incorporated in a controlled $O_2$ permeable bag.

SUMMARY OF THE INVENTION

Figure 5:
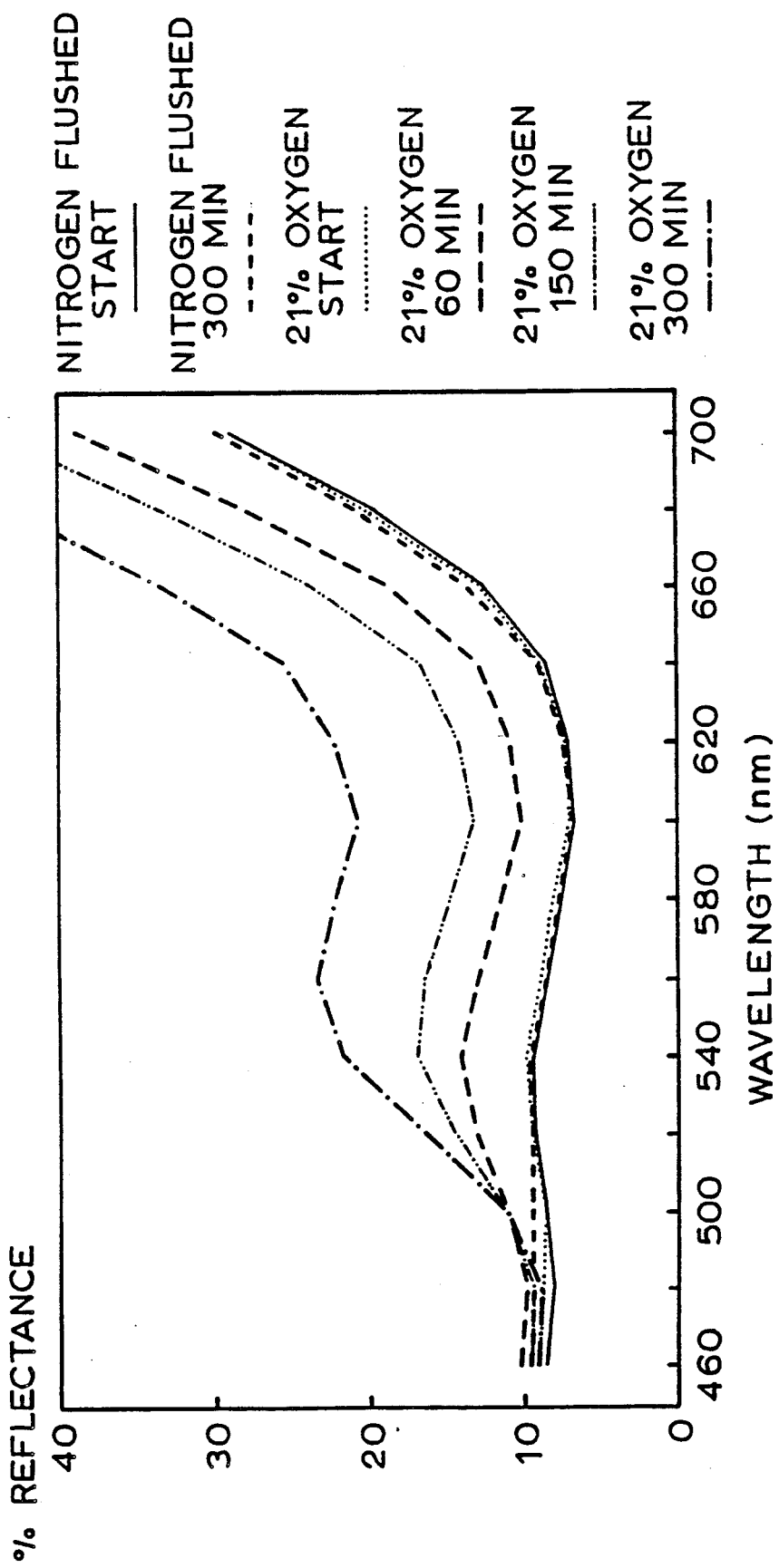
FIG. 5 is a reflectance scanning graph of methyl linolenate sensors as produced in Example I and held at 21° C. under various conditions.

The present invention comprises a system for visually detecting loss of package integrity of a sealed package due to the exposure of a sensor therein to oxygen after the package and sensor have been sealed under an inert atmosphere. The sensor is sufficiently insensitive to the effect of oxygen that it is operative even when prepared in the presence of oxygen or air and then incorporated into a package followed by inert gas flushing and sealing, while it is also sufficiently sensitive to oxygen to undergo a significant color change in about one to eight hours following contamination of the inert package headspace with oxygen or air. Moreover, the sensor is unaffected by the presence or absence of reducing agents in, or used to produce, the product being packaged unless a redox indicator, like methylene blue, is used.

DETAILED DESCRIPTION OF THE INVENTION

The present visual detection system comprises one or more compounds which are unaffected by contact with reducing agents and which will cause an indicator to change color when the compounds are exposed to a sufficient amount of oxygen. The compounds useful herein may undergo oxidation which by itself will cause the associated indicator to change color, or they may undergo oxidation followed by decomposition of the oxidative product to cause the color change, or the compounds may act on the indicator to change its color, but only after the oxygen sensitive compounds have been peroxidized in a reaction in which, e.g. an enzyme, plays a catalytic role. In each case, the introduction of oxygen into a sealed previously essentially oxygen-free environment will cause a sufficient color change of the visual sensor to be readily apparent to even a casual observer The individual components of the system as well as combinations thereof and decomposition products, if any, may be selected to be non-toxic to man. Also the components do not deleteriously interact with the contents of the package, are stable under anaerobic conditions, and do interact with each other and oxygen in a controlled and controllable manner.

Referring to the drawings, FIGS. 1 and 2 show a colorimetric indicator system 10 which comprises a support 12, a color indicator 14, and an oxygen sensitive material 16 which upon extended exposure to oxygen will cause the color indicator to change color. A colorimetric indicator may be prepared by depositing or applying the chosen color indicator 14 on at least a portion of the support 12. This operation may be performed either aerobically or anaerobically. Then an oxygen-sensitive material 16 is deposited or applied to the support 12 either along side or, more preferably, atop the color indicator 14. This operation may be performed anaerobically or, more preferably, aerobically provided that the oxygen-sensitive material is sufficiently insensitive to oxygen, as described further below. Alternatively, the color indicator and the oxygen-sensitive material may be placed together into a deoxygenated solution, preferably along with a thickener or emulsifier, and jointly deposited upon the support 12. After the depositing, the indicator system 10 is then ready for insertion into an at least partially translucent, substantially gas impermeable package 18, wherein the contents (not shown) are to be maintained in a substantially anaerobic state. If the oxygen-sensitive material has been deposited anaerobically due to its oxygen sensitivity, then the insertion should be performed anaerobically. However, if the oxygen-sensitive material can be deposited aerobically, then the insertion may also be performed aerobically followed by extensive flushing with copious amounts of inert gas prior to sealing. Sealing of the container is performed anaerobically with a closure means 20 which is substantially gas impermeable. In such a case it will generally be desirable to incorporate a flexible, substantially gas impermeable septum 22 between the package 18 and the closure means 20 for use in flushing with a canula. Alternatively, the septum may be omitted if equipment is available for gas flushing of containers to less than about 0.5%, preferably less than about 0.1% oxygen.

As indicated, the indicator system takes the form of the support 12 which, after deposition of the color indicator 14 and the oxygen-sensitive material 16 is placed in, or more preferably attached to an inside wall of, an at least partially translucent air-tight package, generally comprised of glass or clear plastic. As suggested, the package may have opaque portions, such as the sides, and need not be completely translucent when the indicator is affixed, for example, to a translucent package bottom or a "window" in a package side or beneath a translucent cap. Generally the support will be used in the form of a strip about 1" by 0.5". The suport or a portion of it may be coated uniformly with the color indicator as shown in FIGS. 1 and 2, or the color indicator may be printed thereon to have a conventional barcode pattern as shown in FIG. 3A. When the color indicator printed bar-code pattern of FIG. 3A is used as the indicator system and it is exposed to oxygen, the bar-code pattern will become unreadable as shown in FIG. 3B.

Suitable color indicators useful herein include well-known materials such as pH indicators like neutral red, hematoxylin, brazilin, lacmoid, carminic acid, nitrazine yellow, curcumin, bromothymol blue, methyl orange, propyl red, phenol red, bromocresol purple, alizarin, and the like. The pH indicators should generally be effective in the pH range of about 4.5 to 9. pH indicators such as litmus and methyl red, while useful herein, are useful only for products not containing reducing agents which could cause reductive color loss. Alternatively, carotinoid pigments such as beta-barotene and lycopene could be used since they have been known to change color upon oxidation. Further alternatively, the color indicator may be a combination of two or more compounds, such as 3-methyl-2-benzothiozolinone hydrazone (MBTH) and 3-(dimethylamino)-benzoic acid (DMAB) which are colorless but which react in the presence of peroxides to yield a deep blue color. Another combination of useful compounds include benzophenol and tetrahydrofuran which are colorless but react in the presence of metallic sodium and oxygen to produce a bright blue ketyl. Use of color indicators composed entirely of natural, FDA approved ingredients like curcumin and carminic acid, which have indicator properties in the proper pH range for this reaction, is highly desirable.

Nitrazine yellow is a preferred color indicator because of its excellent long-term resistance to both light fading and the effects of peroxidation during the degradation of polyunsaturated lipids under the influence of oxygen. It changes color from dark blue-green or blue to bright yellow-orange after exposure to air and an oxygen-sensitive material such as unsaturated fatty acid esters. As shown below in Example I, large differences in reflectance at 540–640 nm are noted between control sensors maintained under anaerobic conditions and sensors exposed to oxygen for a few hours.

Suitable support materials are essentially non-reactive, neutral and non-buffering, porous, oil-absorbent materials such as paper, cardboard, or synthetic or natural polymeric materials such as polystyrene or polypropylene, or films formed from neutral starches or gums having low ion exchange and buffering capacity. Generally any material may be utilized as a support provided that is does not interfere in the interaction between the color indicator and the oxygen-sensitive material, though most conveniently it can be white laboratory filter paper such as Whatman's TM 1 paper. Contact between the support material and with human skin or other sources of organic acids should be avoided.

With regard to suitable oxygen-sensitive materials, they are materials which either react fairly rapidly with oxygen at low partial pressures or react rapidly with the color indicator in the presence of oxygen at low partial pressures. For example, long-chain unsaturated esters, preferably containing methylene-interrupted carbon-carbon double bonds, such as methyl linoleate or methyl linolenate or methyl arachidinate will, upon exposure to oxygen, undergo relatively rapid peroxidation and then decomposition to yield reaction products which have increased acidity and will reduce the pH in the area of the color indicator and, if the color indicator is properly chosen, change its color. Suitable such esters are those which are relatively non-volatile below about 60° C. and contain about 4 to 24 carbon atoms, preferably about 8 to 20, in the fatty acid body of the molecule and about 1 to 3 carbon atoms, preferably 1, in the ester grouping. They may have up to about 4 double bonds, though preferably only 2 or 3 as the sensitivity to exposure to oxygen increases with the number of double bonds. Mono, di and tri-glycerides containing large proportions of esterified polyunsaturated fatty acids in their compositions are also appropriate. Many liquid waxes and glyceryl-ether lipids are also effective provided they are composed primarily of polyunsaturated fatty hydrocarbons with methylene-interrupted double bonds. Alternatively, the esters could be used with carotinoid pigments which are not pH sensitive but which are readily oxidizable in the presence of the peroxides which initially form upon exposing the esters to oxygen. Still further alternatively, the esters could be replaced with other compounds which would react with oxygen to form hydroperoxides (peroxidation) which would then decompose to yield a relatively more acidic material. Such other compounds could include carbonyls, alcohols and the like. Methyl and ethyl linolenate are particularly preferred because of their relatively rapid reaction with oxygen, low cost, and availability in highly purified form.

In addition to the above compounds, the oxygen-sensitive material may comprise an enzyme in combination with a polyunsaturated fatty acid, generally in a suspension. For instance, lipoxygenase (lipoxidase), from plants such as soybeans, in the presence of linoleic acid will bleach an orange carotene mixture white in a short time under appropriate conditions. Alternatively, the enzyme peroxidase, derivable from horseradish or fig trees, can be used to accelerate the reaction of peroxides with MBTH and DMAB to convert a colorless system to a deep blue.

Still further oxygen-sensitive materials useful herein are those aldehydes which are easily oxidized in air to their corresponding carboxylic acids. A preferred aldehyde is benzaldehyde since both it and the benzoic acid to which it oxidizes are approved for food use in limited quantities.

Depending upon the degree of oxygen sensitivity of the specific oxygen-sensitive compound used, it may be desirable to incorporate a catalyst to increase the speed of the reaction with oxygen. Bovine hemin is an acceptable catalyst for lipid oxidation at about 23 to 340 mg/liter indicator solution, and can be solubilized readily in slightly alkaline aqueous methanol, ethanol or isopropanol. It cannot be solubilized in anhydrous solvent. Hemoglobin, myoglobin and cytochrome c are also highly effective catalysts for lipid oxidation, but it has been difficult to solvate them in the preferred indicator system. Chlorophyll and its degradation products are also catalytic for the oxidation of unsaturated lipids. Other materials which are catalytic in the specific system may be used in place of these catalysts. When used, the catalyst will generally be mixed with the color indicator and deposited on the support simultaneously therewith.

To prepare the visual indicator system of the present invention, a suitable support material is selected, a color indicator is deposited thereon, an oxygen-sensitive material is applied thereto, and the coated support is inserted into the package being protected either aerobically followed by flushing of the sensor and the package with an inert gas prior to sealing or under total anaerobic conditions.

Generally, the color indicator will be applied in the form of a solution, e.g. a printable ink. The solution may be aqueous or non-aqueous depending upon the solubility of its components. Preferably a combination of water and an alcohol, such as isopropanol due to its low inherent acidity, are used when catalysts, such as bovine hemin, which are insoluble in anhydrous solvents are used. Other suitable solvents include methanol and ethanol. To prepare the color indicator solution it has oftentimes been found helpful to include a base such as sodium or potassium hydroxide and to use an elevated temperature to assist in the solubilization.

Assembly of the basic sensor is then completed by application of a small amount of an oxygen-sensitive material which is unstable to and reacts with oxygen. Once activated by the deposition of the oxygen-sensitive material, the sensor is positioned in the package and flushed thoroughly with inert gas to prevent premature onset of oxidation and corresponding color change of the color indicator. Alternatively, the prepared sensor may be flushed with inert gas and then stored anaerobically for later use. Still further alternatively, the oxygen-sensitive material may be applied under anaerobic conditions and directly inserted into an anaerobic package without the flushing.

As indicated, application of the oxygen-sensitive material need not be performed under anaerobic conditions so long as the completed indicator is placed into its package and flushed thoroughly with copious amounts of inert gas before any substantial reaction with atmospheric oxygen occurs. For instance, exposure of methyl linolenate-based sensor systems to air for one minute did not affect the performance of control indicators kept subsequently under nitrogen for several days. Twenty volumes of inert gas, i.e. nitrogen, argon and the like, have been found to be sufficient to purge oxygen from a package provided that the gas is introduced through a canula or similar device into the bottom of the package and exhaust is vented through the top, which can easily be done by using a flexible septum, or innerseal, and beveled canulae, and avoids trapping of oxygen in stagnant areas. After flushing, a lug cap may be fitted which has very high oxygen barrier properties. The production of package units incorporating the visual indicators of the present invention may be made with no substantial modification of existing packaging equipment for conventional gas flushing of oxygen-sensitive products.

Once substantially all oxygen has been removed from contacting the sensor, a constant, stable color will show throughout the established shelf-life of the packaged product, provided that no or very little oxygen or atmospheric gas enters the package, either by accident or design. Should the package be compromised such that oxygen contaminates the product headspace, a chemical reaction will begin to take place on the sensor leading to significant changes in pH, a large change in indicator color, and, when the oxygen-sensitive material is a preferred lipid, the development of an odor characteristic of oxidizing lipids. These odors provide an important and powerful secondary signal indicating a failure of the package seal.

Color change on the oxygen exposed indicator strip can also be combined with bar-code scanning technology to develop a means of spotting packages at point of sale which have been opened, damaged or tampered with. Thus a preferred system of this invention is prepared by the application of a slightly modified color indicator and optional catalyst system in the form of a printable ink. The ink may be formed by adding a small amount of, for example, hydroxypropyl methylcellulose and it may be patterned to provide bar-coded information upon point-of-sale scanning by low-power laser or other means. When exposed to oxygen, the bar code information will become unreadable by machine and thus store clerks will be forced to look at the package, will discover the color change, and can intercept the product before a customer takes it from the store. A preferred printable ink may be made by adding about 2 to 4% hydroxypropyl methylcellulose to the hot nitrazine yellow indicator solution discussed above. In addition, approximately 5–10 ml 0.2M NaOH should be used in making the dye solution to stabilize the color of the indicator on the support.

An alternative method of preparing the colorimetric indicator system is shown in FIG. 4. In this case the inside of a generally clear oxygen permeable membrane or plastic bag 24 is coated with the desired oxygen-sensitive material 16, a color indicator strip 14 is placed in the bag 24, and the bag is sealed. Further alternatively, a complete indicator system can be placed in bag 24 to totally isolate it from the package contents or to modify the oxygen sensitivity of a particular system by the oxygen permeability of the bag 24. In both cases, the resultant system can then be stored anaerobically for subsequent placement in a package.

Advantageous ways to utilize the present invention may be to either have a bleed through message printed beneath the color indicator, if the indicator turns to an appropriate color, or to provide a comparative color strip with the same hue as the color indicator prior to the admission of oxygen into the system. Of course, the comparative strip would have to be prepared from an ink insensitive to oxidation.

Further preferred details of the present invention are included in the following non-limiting examples in which all parts and percents are by weight unless otherwise specified.

EXAMPLE 1

Whatman #1 filter paper was cut into strips 1" by 2" and immersed for 2 minutes in a color indicator solution containing 34 mg bovine hemin catalyst, 100 mg nitrazine yellow color indicator, 2.4 ml 0.214 M sodium hydroxide and brought to 100 ml final volume with 70% aqueous isopropanol. The strips were dried for 30 minutes and then 20 microliters of pure methyl linolenate was applied under normal atmosphere atop the color indicator. The strips were put quickly into individual clear vials which were each purged of oxygen by passing at least 20 volumes of nitrogen gas through septums in the tops of the vials using canulas reaching the bottom of the vials. The canulas were removed and the vials sealed tightly with Teflon ®-lined lug caps.

The sealed vials containing the indicator systems were held for several hours at 21 and 60° C. Two vial samples at each storage temperature were opened to the air for a few seconds and then immediately recapped; the color indicators in each vial changed from blue-green to yellow-orange. The change was temperature dependent and occurred much faster at 60° C. than at 21° C. The samples opened and kept at 21° C. changed color over a period of 3–5 hours, while those at 60° C. changed color within 30–40 minutes.

To quantitatively evaluate the stability of the visual indicator systems, samples were analyzed by reflectance scanning which showed large differences in the regions between 540 and 640 nm between control samples held under inert gas and samples which had been opened to the air. Little measurable difference was seen between initial control samples and those scanned after many days, irrespective of the storage temperature, provided that package integrity was maintained. At 21° C. reflectance at 600 nm reached 22% after 5 hours and 75% within 24 hours of exposure to air, compared to less than 10% for the control samples. Reflectance values of 20% were obtained at 60° C. after only 40 minutes exposure of the sensors to air, compared to 6% for controls.

After one day, moreover, the fully-developed yellow-orange oxygen sensor showed reflectance at 600 nm of 75% or more and could not be converted back to the blue-green color characteristic of its alkaline range even after immersion in 0.5 molar NaOH. This is probably due to the formation of a highly-crosslinked "skin" of hydrophobic polymers characteristic of drying oils which have been exposed to the atmosphere. This paint-like coating provides a sensor which is not easily alterable after reaction with oxygen.

To further evaluate the colorimetric indicator systems by reflectance scanning, samples were prepared as described above, flushed with nitrogen and then handled as follows:

(a) Nitrogen Flushed Start—sensors then removed from the package and scanned immediately;

(b) Nitrogen Flushed 300 min—sensors then held at 21 or 60° C. for 300 minutes before scanning;

(c) 21% Oxygen Start—sensors then immediately opened to the air for one minute before scanning;

(d) 21% Oxygen 60 min sensors then opened to the air briefly, resealed, and held at 21 or 60° C. for 60 minutes before scanning;

(e) 21% Oxygen 150 min—sensors then opened to the air briefly, resealed, and held at 21 or 60° C. for 150 minutes before scanning; and (f) 21% Oxygen 300 min—sensors then opened to the air briefly, resealed, and held at 21 or 60° C. for 300 minutes before scanning.

Figure 6:
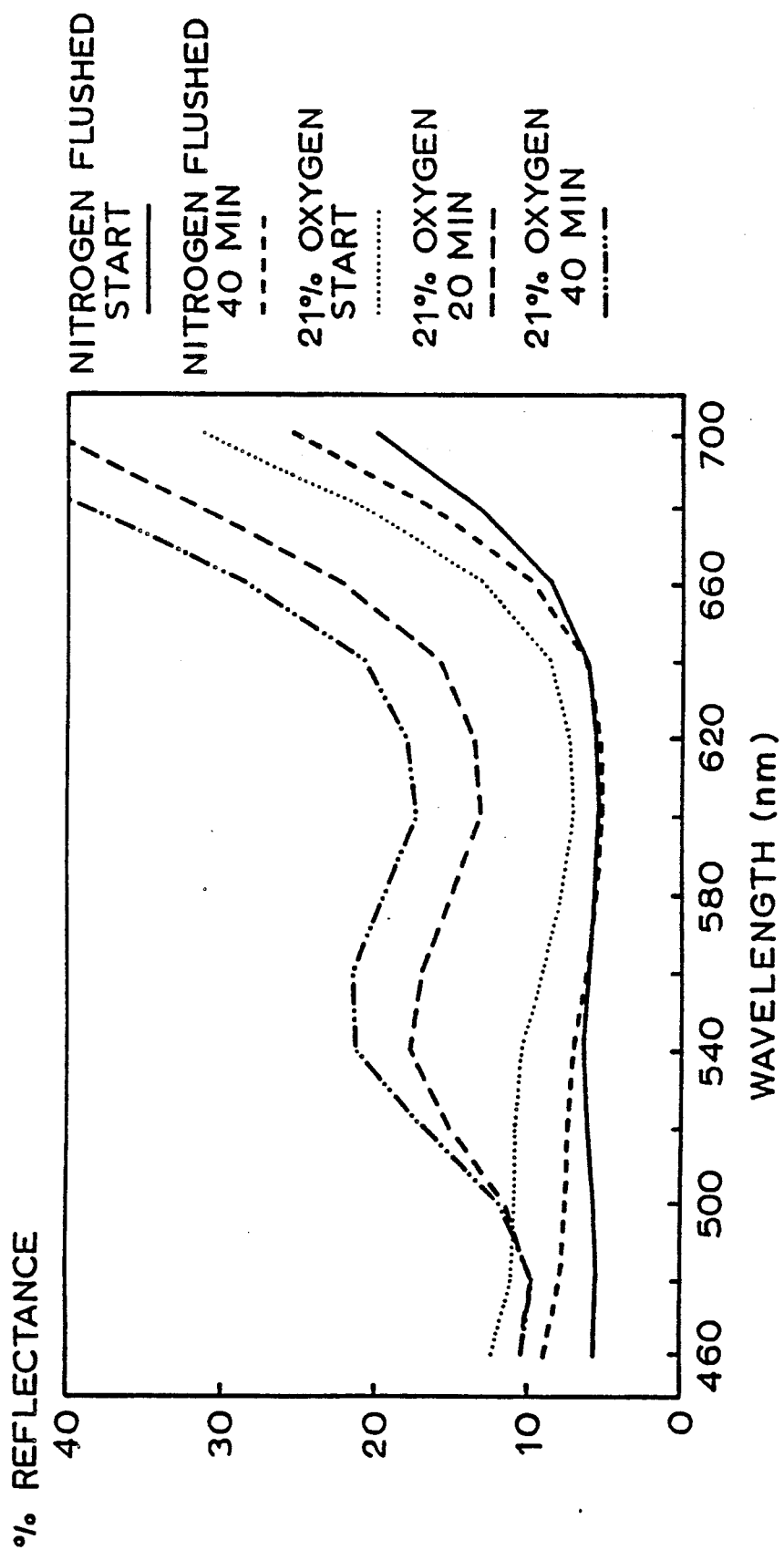
FIG. 6 is a reflectance scanning graph of methyl linolenate sensors as produced in Example I and held at 60° C. under various conditions.

The results of the reflectance scanning tests of samples held at both 21 and 60° C. under the stated conditions are shown in FIGS. 5 and 6 respectively. The results indicate no substantial difference in performance among the control samples held under nitrogen at the start and after 300 minutes or in the test sample after only the briefest, i.e. one minute, exposure to air. Test samples held for longer periods after air contamination, however, show progressive increases in reflectance as a function of time and temperature.

EXAMPLE 2

The procedure of Example 1 was repeated except that 2.2 g of hydroxypropyl methylcellulose and 5 ml 0.214 M NaOH were added to the color indicator solution to form a viscous, printable indicator dye for making a bar-code pattern on the indicator strip. A portion of the strips were printed with a bar-code pattern and then processed as in Example 1 and a portion were laminated between sheets of clear oxygen-permeable plastic film.

The color changes observed after breaking the package seals and exposure of the bar-code sensors to oxygen in both cases occurred in much the same manner and with essentially the same time-temperature response as in Example 1.

EXAMPLE 3

A color solution was prepared as in Example 1, except that only 1 ml NaOH and no indicator dye was added to the solution. Instead of using the filter paper support, strips of 0.5 by 2.0 cm commercial blue litmus paper were dipped into the solution for two minutes and then dried for 30 minutes. 20 microliters of ethyl linolenate was then applied to each strip and the strips placed into clean vials, flushed with nitrogen, and sealed. Color change from blue to pink occurred after breaking the seals and exposing the sensor to atmospheric oxygen. A color change was noticeable in the sensor in 4-6 hours and was complete within 24 hours at 21° C. and within 30-60 minutes at 60° C.

Litmus is subject to loss of color on reduction and this system is therefore useful only in the absence of significant amounts of reducing agents in the package products.

EXAMPLE 4

A color solution was prepared as in Example 1, except that the bovine hemin catalyst was omitted therefrom. The solution was applied to the filter paper and then 50 microliters of pure benzaldehyde was applied thereto. The sensor exhibits the characteristic benzaldehyde almond-like odor. The sensor was then placed into a vial, flushed with nitrogen, and sealed. The resultant blue-green color was stable for extended periods.

Opening of the vial and exposure of the sensor to air caused the color of the indicator to change to yellow-orange within about one hour at 25° C. In addition the samples lost their almond-like odor due to conversion of the benzaldehyde to benzoic acid, both of which are edible to man.

EXAMPLE 5

The procedure of Example 3 was repeated except that the ethyl linolenate was replaced by 50 microliters of benzaldehyde. Sensors so prepared changed from blue to pink within an hour of exposure to air.

EXAMPLE 6

The procedure of Example 4 was repeated except that after preparation of the sensor it was laminated between two pieces of cellophane. The cellophane reduced the almond-like odor and slowed the color change after exposure to air, but the change still occurred within about an hour.

While the invention has been described in detail with respect to certain preferred embodiments thereof, it will be apparent that numerous modifications and alterations may be made which are nonetheless within the spirit and scope of the present invention.

What is claimed is:

1. A colorimetric indicator system to warn of tempering in a sealed package comprising (a) an oxygen-sensitive compound and (b) a separate color indicator which (i) will change color in response to an interaction between oxygen and the oxygen-sensitive compound and (ii) will not change color in direct response to oxygen.

2. The system of claim 1, wherein the color indicator is selected from the group of color indicators which are unaffected by a reducing agent.

3. The system of claim 1, wherein the interaction between oxygen and the oxygen-sensitive material causes a change in the pH of the system.

4. The system of claim 1, wherein the oxygen-sensitive material is sufficiently insensitive to oxygen that the system is prepared in an aerobic environment and then transferred into an anaerobic environment with flushing of all oxygen therefrom for use.

5. The system of claim 4, wherein the system is sufficiently sensitive to oxygen that it changes color within about 1 to about 8 hours of exposure thereto.

6. The system of claim 1, wherein the oxygen-sensitive material undergoes peroxidation in the presence of oxygen.

7. The system of claim 6, wherein the peroxidized oxygen-sensitive material undergoes decomposition to produce a more acidic material than the oxygen-sensitive material.

8. The system of claim 7, wherein the more acidic material induces the color change of the color indicator.

9. The system of claim 8, wherein the color indicator is selected from the group consisting of neutral red, hematoxylin, brazilin, lacmoid, carminic acid, nitrazine yellow, curcumin, bromothymol blue, litmus, methyl red, methyl orange, propyl red, phenol red, bromocresol purple, and alizarin.

10. The system of claim 1 wherein the oxygen-sensitive material is an unsaturated $C_1$–$C_3$ ester of a fatty acid having about 4 to about 24 carbon atoms.

11. The system of claim 10, wherein the oxygen sensitive material is selected from the group consisting of methyl linoleate, methyl linolenate, and ethyl linolenate.

12. The system of claim 1, wherein the color indicator is selected from the group consisting of neutral red, hematoxylin, brazilin, lacmoid, carminic acid, nitrazine yellow, curcumin, bromothymol blue, litmus, methyl red, methyl orange, propyl red, phenol red, bromocresol purple, and alizarin.

13. The system of claim 1, wherein the color indicator comprises a carotinoid pigment.

14. The system of claim 1, wherein the oxygen-sensitive material is an unsaturated $C_1$–$C_3$ ester of a fatty acid having about 4 to about 24 carbon atoms and the color indicator changes color due to a change in acidity.

15. The system of claim 1, wherein the oxygen-sensitive material is an aldehyde and the color indicator changes color due to conversion of the aldehyde to an acid.

16. The system of claim 15, wherein the aldehyde is benzaldehyde and it converts to benzoic acid.

17. The system of claim 14 wherein the interaction between oxygen and the oxygen-sensitive material is catalyzed by a lipoxidase or peroxidase enzyme.

18. The system of claim 14 comprising peroxidase, 3-methyl-2-benzothiozolimone hydrazone and 3-(dimethylamino)-benzoic acid which combine to yield a bluish color in the presence of oxygen.

19. The system of claim 1, having the form of a universal bar-code pattern which becomes unreadable by machine after exposure to oxygen.

20. The system of claim 1, wherein the interaction between oxygen and the oxygen-sensitive material is catalyzed by the addition of a catalyst.

21. The system of claim 20, wherein the catalyst is selected from the group consisting of hemoglobin, myoglobin, hemin, chlorophyll, and cytochrome c.

22. The system of claim 1, wherein the color change is irreversible.

* * * * *